United States Patent [19]
Gundlapalli et al.

[11] Patent Number: 5,697,933
[45] Date of Patent: Dec. 16, 1997

[54] BONE-TENDON-BONE DRILL GUIDE

[75] Inventors: Ramarao Gundlapalli; Alan Chervitz; E. Marlowe Goble, all of Logan, Utah

[73] Assignee: MedicineLodge, Inc., Logan, Utah

[21] Appl. No.: 574,398

[22] Filed: Dec. 18, 1995

[51] Int. Cl.[6] ................................................ A61B 17/56
[52] U.S. Cl. ........................... 606/96; 606/206; 606/207
[58] Field of Search .......................... 606/96, 97, 98, 606/86, 88, 90, 79, 102, 206, 205, 207, 208

[56] References Cited

U.S. PATENT DOCUMENTS

| | | |
|---|---|---|
| 4,257,411 | 3/1981 | Cho . |
| 4,535,768 | 8/1985 | Hourahane et al. . |
| 4,668,233 | 5/1987 | Seedholm et al. . |
| 4,672,957 | 6/1987 | Hourahane et al. . |
| 4,739,751 | 4/1988 | Sapega et al. . |
| 4,823,780 | 4/1989 | Odensten et al. . |
| 4,901,711 | 2/1990 | Goble et al. . |
| 4,920,958 | 5/1990 | Walt et al. . |
| 4,985,032 | 1/1991 | Goble . |
| 5,152,764 | 10/1992 | Goble . |
| 5,234,434 | 8/1993 | Goble et al. . |
| 5,314,429 | 5/1994 | Goble . |
| 5,366,457 | 11/1994 | McGuire et al. . |
| 5,385,567 | 1/1995 | Goble . |

FOREIGN PATENT DOCUMENTS

| | | |
|---|---|---|
| 0126520 | 11/1984 | European Pat. Off. . |
| 2078528 | 6/1980 | United Kingdom . |

Primary Examiner—Guy V. Tucker
Attorney, Agent, or Firm—M. Reid Russell

[57] ABSTRACT

A bone-tendon-bone drill guide for use is guiding drilling to form a pair of transverse holes through a bone end of a bone-tendon-bone ligament graft to receive a suture or sutures threaded therethrough to form a suture sling or craddle supporting the bone end as the suture are pulled into a tunnel section of a straight that has been formed into a patient's bone. The drill guide includes a pair of scissor arms connected at a pivot that are formed to where moving of lower hand engaging portions of the arms together also moves upper ends of the arms together whereacross opposing jaws are maintained. The jaws each include curved surface therealong for engaging a bone end fitted therebetween and each preferably includes spikes that extend from a jaw face for engaging, to hold in place, the bone end as a drill is turned through straight drill guide holes formed through a jaw to form transverse holes through the bone end, with the drill to exit the bone end and pass through openings formed through the other jaw. To lock the jaws in place, the drill guide further includes a straight brace that is pivotally connected to the lower end of one scissoring arm to pivot an edge thereof into alignment with a single tooth that extends from the bottom end of the other scissoring arm, the straight brace including a series of teeth formed along its edge to engage the single tooth and is spring biased to urge the series of teeth against the single tooth, urging a meshing engagement therebetween.

9 Claims, 3 Drawing Sheets

5,697,933

1
BONE-TENDON-BONE DRILL GUIDE

BACKGROUND OF THE INVENTION

1. Field of the Invention

This invention relates to surgical devices and in particular to drill guides as are used in arthroscopic surgical procedures for forming transverse holes in a bone end of a ligament graft for use, as for example, in knee ligament reconstruction surgery.

2. Prior Art

The invention, is another of a number of earlier drill guides of one or more of the inventors, except that the present drill deals with a device and its use for forming a transverse hole or holes through a bone end of a bone-tendon-bone type ligament graft. Such hole formation is for passing a suture through the formed hole or holes to create a suture sling, craddle, or the like, that connects to the bone end to allow an operator who pulls on the suture ends threaded through a ligament tunnel, to move ligament graft into a desired location in that ligament tunnel. Such ligament tunnel will have been formed utilizing such earlier drill guides, for example, like one of those shown in U.S. Pat. No. 4,901,711; in U.S. Pat. No. 4,985,032; in U.S. Pat. No. 5,152,764; and in U.S. Pat. No. 5,234,434 of at least one of the inventors. Similarly, though not directly relating to the invention, a number of earlier drill guides have been used in knee arthroscopic surgical procedures for drilling, from without the knee, to a locator point within the knee intra articular joint. Examples of such earlier drill guides are shown in patents to Hourahane, et al, U.S. Pat. No. 4,535,768; and U.S. Pat. No. 4,672,957. Additionally, other earlier drilling devices have been developed for drilling or forming intersecting holes or passages to select locations along a tunnel section or sections at angles in a range of angles that are greater and lesser than ninety (90) degrees, with examples of such a device shown in a patent to Odensten, et al, U.S. Pat. No. 4,823,780. These types of drill guides, unlike the invention, have been used in an anterior or posterior cruciate ligament repair and/or replacement surgical procedure where tibial and femoral tunnel sections are formed in the distal femur and proximal tibia to pass through the ligament points of origin, which tibial and femoral tunnel sections with the knee bent appropriately, are straight and will conveniently accommodate threading of suture ends therethrough to pull a ligament end to a location within such tunnel section.

Heretofore, it has been common practice for a person preparing the ligament graft harvested from a patient to manually holding a bone end and, with a hand held drill, drill a pair of small diameter transverse holes by eye to have a desired spacing distance apart and from the bone end. Such practice, of course, has often resulted in damage to the bone end that slips out from the operators grasp, and has resulted in holes that are not aligned or are not properly spaced. Recently, an attempt has been made to stabilize such bone end during drilling by fitting it into a slot or groove formed in a block, and compressing the bone end with a compression plate wherein holes are formed that an operator drills through to form one or more transverse holes. Such an assembly is shown in U.S. Pat. No. 5,366,457. This arrangement, however, does not provide a device like that of the invention that has scissor arms with opposing jaws that are moved together by an operator squeezing the arms together to easily and surely grip the bone end, which opposing jaws can be locked in place allowing an operator to releasing their gripping pressure. The jaws to include drill guide ports that an operator drills through to form exactly positioned and properly spaced transverse holes through the bone end.

SUMMARY OF THE INVENTION

It is a principal object of the present invention in a bone-tendon-bone drill guide to provide a manually operated device that has opposing jaws that are moved together for clamping onto a bone end of a bone-tendon-bone ligament graft, which jaws include drill holes or ports for turning a drill through to form appropriately positioned and properly spaced transverse holes through the bone end.

Another object of the present invention is to provide a bone-tendon-bone drill guide that has opposing jaws that can be locked together for maintaining a bone end of a bone-tendon-bone ligament graft therebetween providing for both drilling a pair of spaced transverse holes through the bone end and for use in determining the bone end diameter Another object of the present invention is to provide a bone-tendon-bone drill guide that provides opposing jaws with one or more spikes extending from opposing jaw surfaces for aiding gripping and maintaining a bone end of a bone-tendon-bone ligament graft therebetween while a drill is turned through aligned drill holes or ports formed in the opposing jaws, forming transverse holes through the bone end.

Still another object of the present invention is to provide a bone-tendon-bone drill guide that is easy and safe to used to guide drilling of a pair of transverse holes through a bone end of a bone-tendon-bone ligament graft.

The bone-tendon-bone drill guide of the invention provides a device a pair of pivotally connected scissoring arms with opposing curved jaws secured to ends thereof that are moved together to grip a cylindrical and trapezoidal bone end of a bone-tendon-bone ligament graft therebetween. The opposing jaw curved surfaces preferably each include one or more spikes extending outwardly therefrom to fit into so as to hold the bone end in position as a drill is turned through each of a pair of drill guide holes formed in one jaw. The drill is turned through the drill guide hole, forms a transverse hole through the bone end and exits an open area formed through the other jaw. Whereafter, the jaws are released and moved apart, releasing the bone end that can then receive a suture or sutures threaded through the transverse holes to form a sling craddle, or the like, connecting the suture or sutures to the bone end. The ends of the sutures can then be threaded and pulled through a bone tunnel, pulling the following ligament graft bone end therein.

Further, for both facilitating maintaining the opposing jaws in clamping arrangement against the bone end, the device of the invention preferably includes a ratchet locking mechanism consisting of a brace that is pivotally coupling to the end of a lower portion of one arm that includes spaced teeth formed therealong. The teeth are arranged for sliding over a single tooth that extends from the end of the other arm lower portion, the respective brace teeth sliding over the single tooth as pressure is applied to a bone end that is clamped between the opposing jaws, as by applying pressure to the arm lower portions, pivoting the jaws together. Where a desired clamping pressure is exerted until the curved jaw surfaces become congruent on the bone end is obtained, that pressure is maintained by the tooth to tooth engagement of one of the brace teeth and the single tooth. This pressure is maintained until the brace is pivoted away from the single tooth. Preferably, to facilitate maintenance of contact between the brace teeth and single tooth, the pivot includes a spring for biasing the brace toward the single tooth. Additionally, markings indicative of distances diameters, preferably in millimeters, can be scribed at appropriate intervals along the brace. Thereby, as the brace travels over the single tooth, closing the jaws together, the marking opposite to the tooth will indicate the spacing distance between the opposing jaws surfaces, that is essentially the diameter of the bone end. Also, as required, markings can be scribed as a scale along one or both jaw edges for comparison with the bone end for measuring a distance therealong or computing the bone end length.

THE DRAWINGS

These and other objects and features of the invention in a bone-tendon-bone drill guide will become more fully apparent from the following description in which the invention is described in detail in conjunction with the accompanying drawings:

FIG. 1 is a profile perspective view of the bone-tendon-bone drill guide of the invention shown as having scissoring arms with a brace that is secured by a pivot to one arm lower end, the brace for pivoting from a broken line to solid lines to extend across the scissoring arms lower ends, aligning teeth formed along the brace with a single tooth shown as extending outwardly from the other arm end and showing opposing jaws secured across the scissoring arms top ends;

Figure 1:
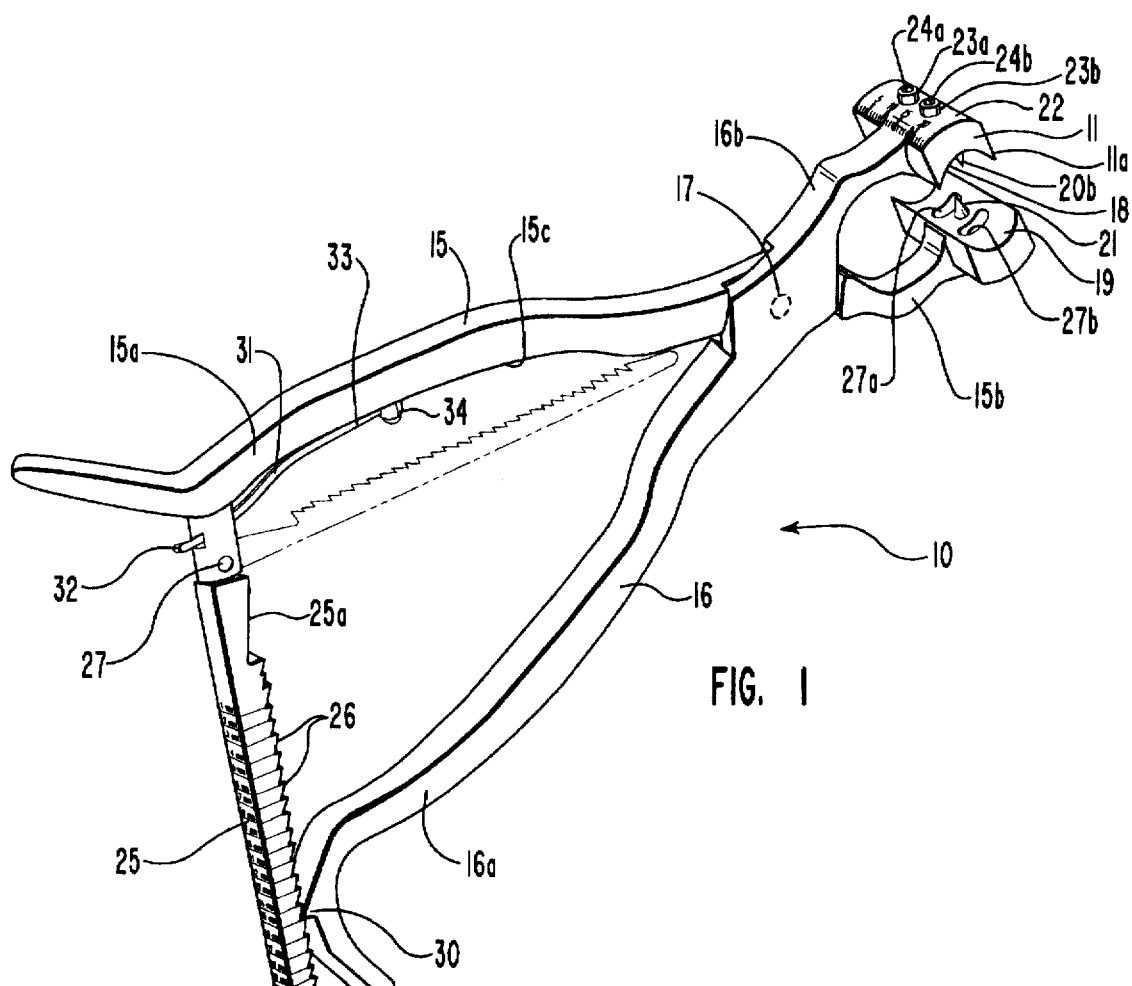
Figure 5A:
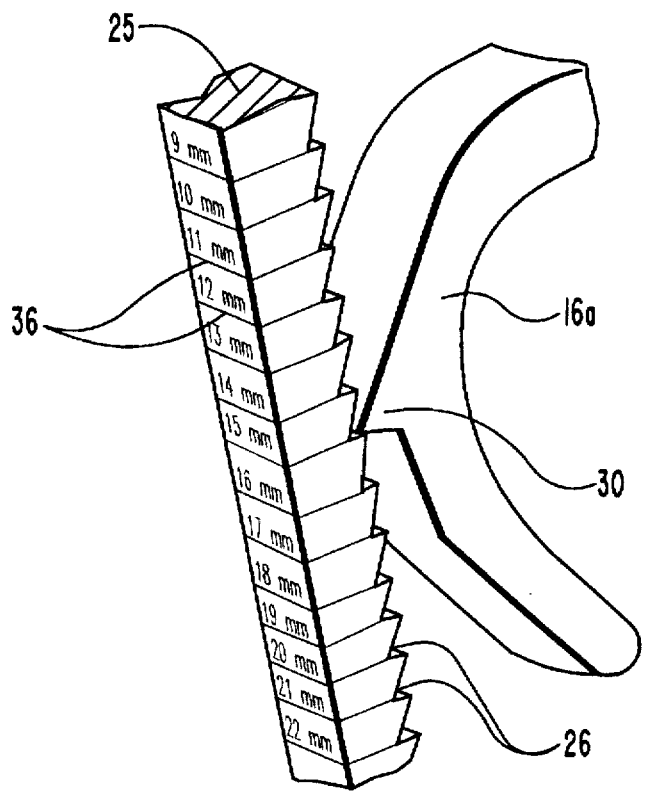
Figure 5B:
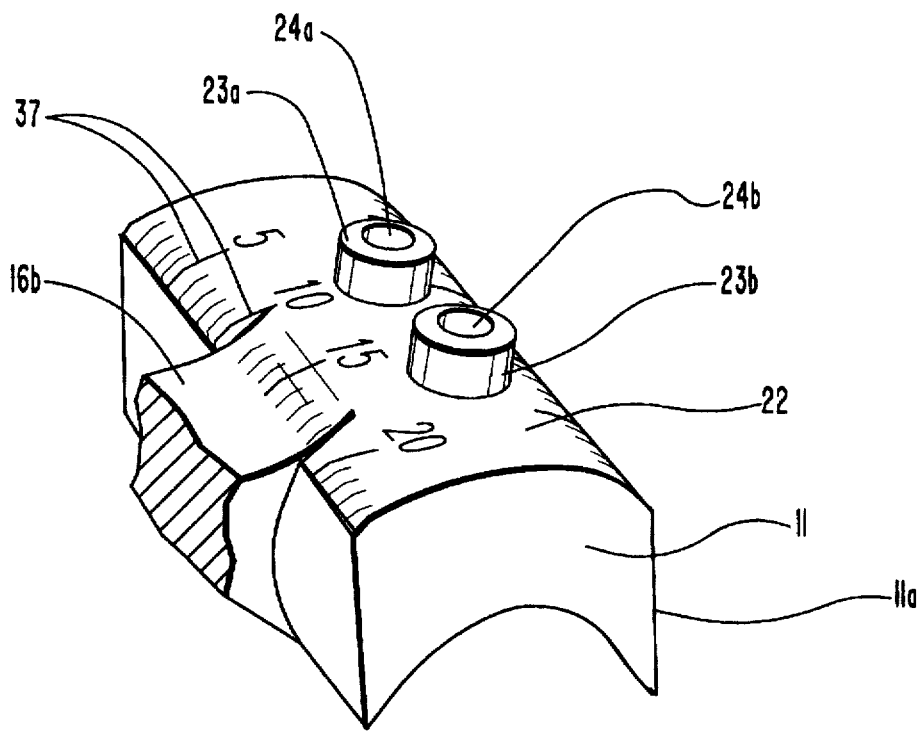

FIG. 5A shows an enlarged section of the brace of the drill guide of FIG. 1 as having markings scribed at intervals therealong with the single tooth aligned with a marking indicative of spacing between the drill guide opposing jaws; and FIG. 5B shows an enlarged section of one of the opposing jaws showing markings scribed at intervals along the edge of the jaw for measuring a distance along or the length of a bone end.

DETAILED DESCRIPTION

Figure 2:
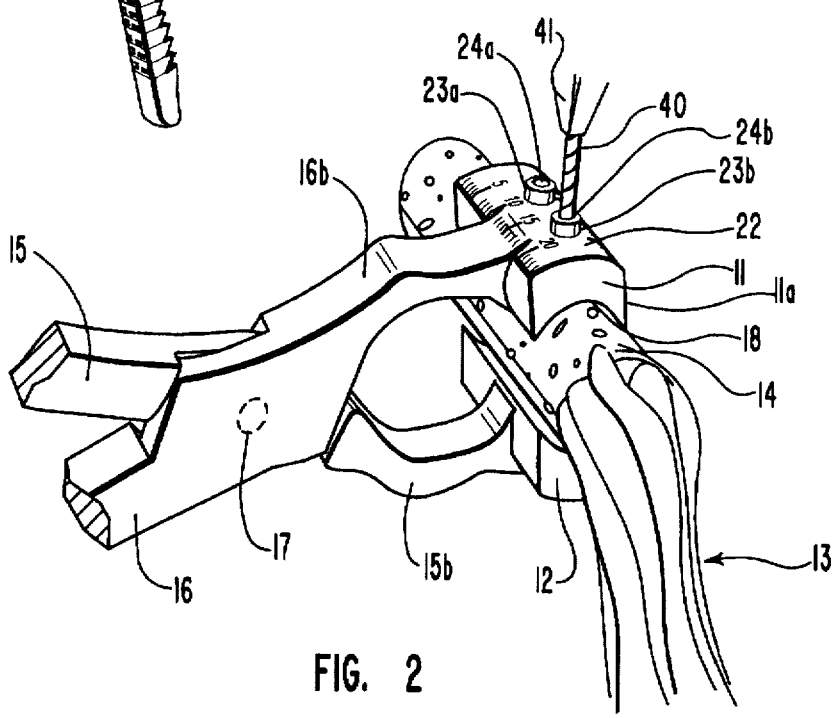
FIG. 2 is a enlarged perspective view of the jaws and top portions of the scissoring arms of the drill guide of FIG. 1, showing the jaws clamped against a bone end of a bone-tendon-bone ligament graft, and showing a drill being turned through one of a pair of drill guide holes formed through one of the jaws.
Figure 3:
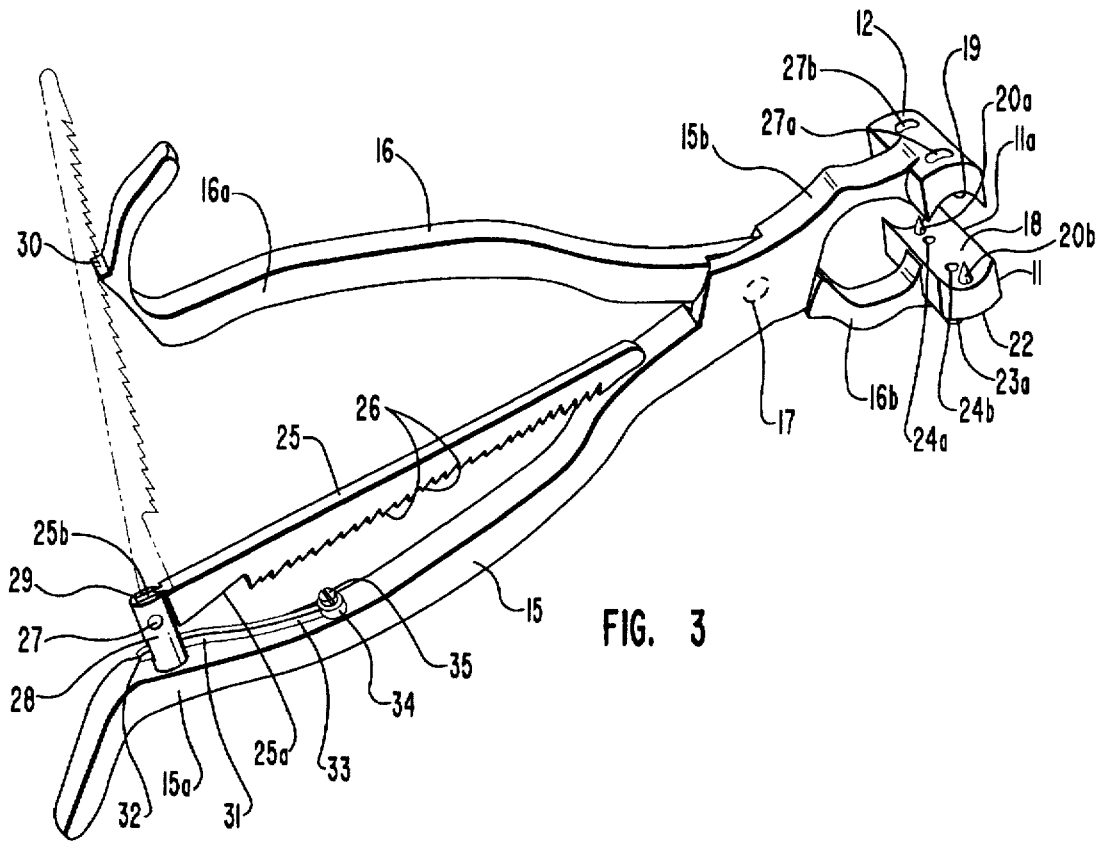
FIG. 3 shows the drill guide of FIG. 1 as a perspective view that has been rotated one hundred eighty (180) degrees with the pivoting brace shown pivoted from a broken line to solid line view to be alongside a lower portion of the arm whereto it is pivotally coupled.
Figure 4:
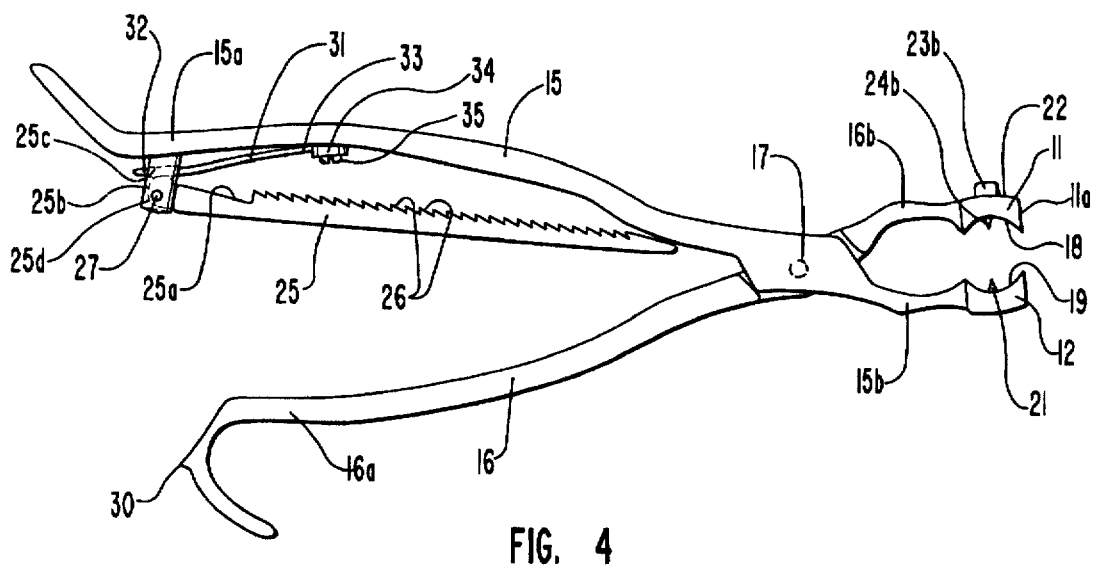
FIG. 4 is a side elevation view of the drill guide of FIG. 1 showing the brace as having been pivoted to a retracted attitude.

FIGS. 1, 3 and 4 show a same embodiment of a bone-tendon-bone drill guide 10 of the invention, hereinafter referred to as drill guide, with opposing jaws 11 and 12 thereof shown close together in FIG. 2 gripping a bone end 14 of a bone end of a ligament graft 13 therebetween. The bone end 14 is preferably an end portion of a bone-tendon-bone ligament graft, but may be a bone-tendon graft, or the like. A pair of arms 15 and 16 are pivotally connected together at a pivot 17, that is shown in broken lines, to provide a scissoring arrangement. Thereby, when arm lower or bottom portions 15a and 16a are moved together, upper portions 15b and 16b of the respective arms will be moved together, the arm upper portions, across their ends, are shown as mount the respective jaws 12 and 11. The jaws 11 and 12, when closed, as shown in FIG. 2, are to clamp against the bone end 14.

Outwardly extending spikes 20a, 20b, and 21 are secured to extend at approximately right angles from opposing curved inner surfaces 18 and 19 of the respective jaws 11 and 12, as shown in FIGS. 1, 3 and 4. So arranged, when the jaws are moved into clamping engagement with the bone end 14, the spikes will enter the bone end surface to hold it in place during drilling. For drilling the bone end 14, as shown in FIG. 2, a pair of spaced collars 23a and 23b are secured at spaced points along, the longitudinal axis of a top surface 22 of the jaw 11, and drill holes 24a and 24b are formed therethrough, exiting the jaw 11 curved inner surface 18. So arranged the drill holes 24a and 24b guide turning of a drill 40 that is shown mounted in a chuck 41 to pass through the bone end 14 and exit through drill exit openings 27a and 27b formed through the jaw 12. Which exit openings 27a and 27b, as shown, are preferably significantly larger than the drill holes 24a and 24b, and are elongate to insure that the drill 40 end will pass therethrough without contacting jaw 12, at any given bone end 14 diameter.

While an operator holding the bottom portions 15a and 16a of arms 15 and 16 can securely maintain the jaws 11 and 12 clamped to the bone end 14 for drilling a pair of holes therethrough, it is preferred to provide a mechanism to maintain this clamping action. Such holding mechanism is preferably provided as a brace 25 that is shown to have a saw blade appearance in the side view elevation, with a series of spaced teeth 26 formed along an inner surface 25a that slope towards an inwardly stepped end 25b. As shown best in FIG. 3, the brace stepped end 25b is fitted into a longitudinal slot 29 that is formed in an end of a post 28, the sides of the stepped end and walls of slot 29 to fit together as shown, and receive a pivot 27 fitted therethrough. So arranged, the brace 25 is allowed to rotate from a stowed attitude, shown in solid lines in FIGS. 3 and 4 and in broken lines in FIG. 1, to an erected attitude shown in solid lines in FIG. 1 and broken lines in FIG. 3. In which erected attitude the brace teeth 26 will slide along a single tooth 30 that, as shown in FIGS. 1, 3 and 4, extends outwardly from a curved portion of the arm 16 bottom portion 16a. The brace teeth 26 will thereby ratchet along the tooth 30 to where a required clamping pressure is applied to the bone end 14, as illustrated in FIG. 2. Thereat, a vertical surface of a brace tooth 26 that aligns with the single tooth 30, will slide over the single tooth 30 vertical surface, locking the arms 15 and 16 in place. The arm 15 and 16 coupling by brace 25 is maintained until an operator lifts the brace away from the single tooth 30 against a spring biasing. Whereafter the arms 15 and 16 are spread apart, releasing the clamping pressure exerted by jaws 11 and 12 on the bone end 14, to allow the brace to be pivoted to a stowed attitude, as shown in solid lines in FIGS. 3 and 4.

To provide the spring biasing whereby the brace 25 teeth 26 are urged against the single tooth 30, as shown in solid lines in FIG. 1 and broken lines in FIG. 2, a spring rod 31 is maintained to an undersurface 15c of the arm 15, shown in FIG. 1. The spring biasing is provided by a spring rod 31 outer end portion 32, shown in broken lines in FIG. 4, that is fitted through post 28 to be adjacent to the slot 29, and in contact with a rounded or cam end 25c of the brace 25. To maintain the spring rod 31 to the arm 15 undersurface 15c, a top end portion 33 of the spring rod 31 is fitted through a lateral holes formed through a pier 34 secured to extend from the surface 15c that includes an axial hole wherein a belt type fastener 35 is turned to engage and secure in place the spring rod 31 top end portion in the pier 34. So arranged, the spring rod 31 is bent or otherwise formed to resist travel to engage the arm 15 undersurface 15c, and with the spring rod lower end portion 32 in engagement with cam end 25c of the brace 25. Accordingly, as the brace 25 is pivoted to the attitude shown in FIG. 1, the cam end 25c slides along the spring rod lower end portion 32 that flexes outwardly to engage a slightly rounded end section 25d of brace 25. So positioned, the spring rod 31 urges brace 25 teeth 26 into engagement with the single tooth 30, providing a spring biasing thereof. Which spring biasing, as set out above, is overcome by lifting the brace 25 away from the single tooth.

Additionally, as desired, and as shown in FIG. 5A, the brace 25 can include a number of spaced markings 36 scribed thereon. An individual marking 36 to align a straight marking formed across the brace 25 that aligns with the single tooth 30. This marking 36 indicates the distance across the jaws 11 and 12 opposing faces 18 and 19 and is for determining the diameter of the bone end 14 clamped therebetween. Also, as shown in FIG. 5B, spaced markings 37, that are preferably in millimeters, can be scribed at spaced intervals along a top surface of one of the jaws, shown herein and in FIGS. 1 through 4 as top surface 22 that has an edge with side 11a, of jaw 11. The markings 37 are for comparison with the positioning of the bone end 14 clamped between jaws 11 and 12 for determining locations along the bone end for forming the pair of transverse holes therethrough.

A preferred embodiment of the present invention in a bone-tendon-bone drill guide and its use has been shown and described herein. It should, however, be understood that this disclosure is made by way of example only and that variations and modification to the described device and its use are possible without departing from the subject matter coming within the scope of the following claims and a reasonable equivalency thereof, which claims we regard as our invention.

We claim:

1. A bone-tendon-bone drill guide comprising, a pair of scissor arms connected together by a pivot whereby moving together of lower hand engaging portions of said scissor arms moves scissor arm top ends together; a pair of opposing first and second jaw means that are each mounted at approximately their horizontal center to extend across and at approximately a ninety (90) degree angle to a scissor arm top end and each jaw means having a half cylindrical surface formed along its longitudinal axis that are in opposition to one another forming, when said scissor arm top ends are closed together essentially an open cylinder; a pair of parallel drill guide means mounted at spaced points along a longitudinal axis of said first jaw means each having a guide hole formed therethrough with the other or second jaw means including like openings therethrough that each align with one of said drill guide means guide holes and have a greater diameter than each said guide hole; and means for locking in place said scissoring arms after said jaw means have been closed together over an item to be drilled.

2. A bone-tendon-bone drill guide as recited in claim 1, further including spike means mounted to extend outwardly from each first and second jaw means opposing face for engaging a bone end of a ligament graft when said first and second jaw means are closed thereon.

3. A bone-tendon-bone drill guide as recited in claim 2, wherein a pair of spike means are mounted to extend from the first jaw means half cylindrical surface along its longitudinal axis and each is adjacent to one of the drill holes and is proximate to an end of said first jaw means; and a single spike means is mounted in the second jaw means, centered between the openings formed therethrough.

4. A bone-tendon-bone drill guide as recited in claim 1, further including scale markings scribed at spaced intervals along an edge of a top surface of the first or second jaw means.

5. A bone-tendon-bone drill guide as recited in claim 1, wherein the drill guide means are a pair of identical short cylindrical sections that are each secured to an outer or top surface of the first jaw means opposite to its half cylindrical surface wherethrough the guide holes are formed.

6. A bone-tendon-bone drill guide as recited in claim 1, wherein the means for locking the scissoring arms in place is a straight brace that is pivotally connected on one end to a bottom end section of the first of the pair of scissor arms, whereby the straight brace can pivot so as to align a brace edge with a bottom end section of the other or second scissor arm wherefrom a single tooth means extends; and forming a series of teeth means along said brace edge that will travel along said single tooth as the scissoring arms lower hand engaging portions are moved towards one another, with one of said series of teeth to slide into engagement with said single tooth, maintaining the positioning of said scissoring arms and the opposing jaw means.

7. A bone-tendon-bone drill guide as recited in claim 6, further including a spring means for biasing the edge of the straight brace at its pivot coupling to the end of the first scissor arm towards the single tooth that extends from the second scissor arm bottom end section.

8. A bone-tendon-bone drill guide as recited in claim 7, wherein the spring means is straight steel rod that is connected at a bottom end to an undersurface of the first scissoring arm lower portion bottom end, and is bent slightly outwardly therefrom, and includes an upper end that is fitted through an outstanding post that is mounted to said first scissoring arm lower hand engaging portion proximate to the bottom end thereof, the post to include a longitudinal slot formed therein that the straight brace end is fitted into, and includes a pin fitted through aligned holes formed through side of said longitudinal slot and straight brace end as the pivot coupling, the said steel rod upper end to engage a rounded end of said straight brace adjacent to said pivots whereby, when said straight brace is pivoted across said scissoring arms lower portions, said steel rod will provide a spring biasing to said straight brace to urge the straight brace edge wherein the series of teeth are formed against the single tooth.

9. A bone-tendon-bone drill guide as recited in claim 7, further including a section of spaced markings indicative of distance formed along a surface of the straight brace, opposite to a section of the series of teeth that will engage the single tooth that functions as a pointer that aligns with a line from one of each of said spaced markings that is in alignment with one of the series of teeth that said single tooth is in meshing engagement with, said spaced markings to indicate the distance between the jaw means opposing half cylindrical surfaces.

* * * * *